United States Statutory Invention Registration [19]

[11] Reg. Number: H505

Slatkin et al. [43] Published: Aug. 2, 1988

[54] BORON UPTAKE IN TUMORS, CEREBRUM AND BLOOD FROM [$^{10}$B]NA4B24H22S2

[75] Inventors: Daniel N. Slatkin, Bayside; Peggy L. Micca, Patchogue; Ralph G. Fairchild, Setauket, all of N.Y.

[73] Assignee: The United States of America as represented by the United States Department of Energy, Washington, D.C.

[21] Appl. No.: 838,494

[22] Filed: Mar. 11, 1986

[51] Int. Cl.[4] ..... A61N 5/12; A61K 43/00; A61K 41/00

[52] U.S. Cl. ..... 424/1.1; 424/9; 128/1.1

[58] Field of Search ..... 424/1.1, 9; 128/1.1; 604/6, 20, 21

[56] References Cited

PUBLICATIONS

Hatanaka, et al., "A Revised Boron–Neutron Capture Therapy for Malignant Brain Tumors", Z. Neurol., 204, 309–332 (1973).

Tolpin, et al., "Boron Neutron Capture Therapy of Cerebral Gliomas", Oncology 32: 223–246 (1975).

*Primary Examiner*—John F. Terapane
*Assistant Examiner*—J. E. Thomas
*Attorney, Agent, or Firm*—Margaret C. Bogosian; James W. Weinberger; Judson R. Hightower

[57] ABSTRACT

A stable boronated ($^{10}$B-labeled) compound, sodium mercaptoundecahydrododecaborate is infused in the form of the disulfide dimer, [$^{10}$B]$Na_4B_{24}H_{22}S_2$, at a dose of about 200 $\mu$g $^{10}$B per gm body weight. The infusion is performed into the blood or peritoneal cavity of the patient slowly over a period of many days, perhaps one week or more, at the rate of roughly 1 $\mu$g $^{10}$B per gm body weight per hour. Use of this particular boronated dimer in the manner or similarly to the manner so described permits radiotherapeutically effective amounts of boron to accumulate in tumors to be treated by boron neutron capture radiation therapy and also permits sufficient retention of boron in tumor after the cessation of the slow infusion, so as to allow the blood concentration of $^{10}$B to drop or to be reduced artificially to a radiotherapeutically effective level, less than one-half of the concentration of $^{10}$B in the tumor.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BORON UPTAKE IN TUMORS, CEREBRUM AND BLOOD FROM [$^{10}$B]NA4B24H22S2

The U.S. Government has rights in this invention pursuant to Contract Number DE-AC02-76CH00016, between the U.S. Department of Energy and Associated Universities Inc.

BACKGROUND OF THE INVENTION

The nuclear reaction $^{10}B(n,\alpha)^7Li$ has been used in boron neutron capture therapy to cure malignant gliosarcomas implanted in the hind legs of mice [Farr et al., *Int. J. Appl. Radiot. Isotopes,* 19, 459 (1968)]. More recently, this reaction has been used in boron neutron capture therapy to cure spontaneous malignant melanomas in pigs [Mishima et al., *Proc. First Int. Symp. Neutron Capture Therapy,* Eds. R. G. Fairchild and G. L. Brownell, Brookhaven National Laboratory, Report BNL 51730, p. 355, 1983]. The sulfhydryl borane monomer $[B_{12}H_{11}SH]^{2-}$ as the sodium salt is used as a $^{10}B$ carrier for boron neutron capture therapy of malignant human brain tumors [Hatanaka et al., *Modern Neurosurgery,* Ed. M. Brock, Springer, Berlin, p. 122, 1982].

The general principle of boron neutron capture therapy, enunciated in the radiological literature decades ago, is based on the physical property of the boron-10 nucleus to strongly interact with thermal neutrons. This approach to cancer therapy is based on the liberation of high energy ionizing radiation in boron-10 enriched tumor tissue during neutron irradiation. The incident thermal neutrons have a relatively low energy (0.025 eV) which gives rise to a very high energy alpha particle (2.4 MeV) from the $^{10}B(n,\alpha)^7Li$ reaction following neutron capture by boron-10.

The major requirements for successful application of boron neutron capture therapy are: First, there must be a large concentration of $^{10}B$ in all microscopically viable areas of the neoplasm (>15 μg of $^{10}B$ per gm of tumor). This requires that the boron compound be injected through blood vessels rather than directly into the suspected tumor area since the precise dimensions and configuration of the invasive neoplastic process are not clearly delineated from the surrounding normal tissue. Second, a source of neutrons must be available to irradiate the neoplastic area with sufficient numbers of thermal neutrons to cause destruction of cells containing boron-10.

SUMMARY OF INVENTION

Applicants have now shown that the dimer $[B_{24}H_{22}S_2]^{4-}$, which has been known [Wellum et al., *Inorg Chem.,* 16, No. 8, 2120 (1977)] but not worked with clinically, has more favorable properties as a carrier of boron-10 for boron neutron capture therapy than the previously used monomer material, $[B_{12}H_{11}SH]^{2-}$. $[^{10}B]Na_4B_{24}H_{22}S_2$ yields higher tumor:blood and tumor:cerebrum boron concentration ratios than does $Na_2B_{12}H_{11}SH$ when each is infused at the same dose (~200 μg B/gbw) very slowly (~1 μg B/gbw-hr) into tumor-bearing mice. These higher concentration ratios make the dimer useful for boron neutron capture therapy of human brain tumors since such tumors have an imperfect blood-brain barrier and are therefore more accessible to $Na_4B_{24}H_{22}S_2$ than are normal brain tissues.

This invention provides a method to improve the results of radiotherapy of cancer and, in particular, of brain tumors. The stable boronated ($^{10}B$-labeled) compound, [$^{10}B$]-sodium mercaptoundecahydrododecaborate is infused in the form of its disulfide dimer, $[^{10}B]Na_4B_{24}H_{22}S_2$, at a dose of about 200 μg $^{10}B$ per gm body weight. The infusion is performed into the blood or peritoneal cavity of the patient slowly over a period of many days, perhaps up to one week or more, at the rate of roughly 1 μg $^{10}B$ per gm body weight per hour. Amounts of boron-10 thus obtained in the tumor will be about 20 μg per gram of wet tumor weight, and such concentrations are favorable for boron neutron capture therapy.

Use of this particular boronated dimer in the manner or similarly to the manner so described also permits sufficient retention of boron in tumor so that an interval of time can be allowed to elapse after the cessation of the slow infusion before tumor irradiation. During this post-infusion interval, normal tissues will be substantially or partially cleared of excess boron via the blood plasma, the kidneys, and the urine before irradiation of the tumor by slow neutrons. Plasmapheresis or plasma exchange can be used, as required, to hasten this clearance and the clearance of other boron compounds injected for the purpose of boron neutron capture therapy. The blood-brain barrier effectively excludes this boronated dimer from normal brain tissue, some of which is inevitably irradiated by neutrons along with the brain tumor. This exclusion, in association with the clearance of boron from plasma by natural kidney function and/or artificially by plasmapheresis or plasma exchange, effectively reduces the irradiation of normal brain endothelial cells to safe limits. All the aforementioned situations, which together are desirable and will be necessary for successful boron neutron capture therapy of malignant human tumors, do not pertain to existing practice of boron neutron capture radiation therapy in Japan, nor to forms of this type of therapy that have been proposed by other researchers to date.

An additional advantage of this mode of use of the boronated dimer $[^{10}B]Na_4B_{24}H_{22}S_2$ is that the boron is substantially excluded from blood cells, so that clearance of boron-10 from blood plasma alone will be sufficient to effect its nearly complete clearance from the blood that circulates in the vasculature of the normal brain. Such residual boron-10 could otherwise be a source of adverse radiation to the endothelium (the cells lining the blood vessels) of the normal brain and thereby be a potential source of undesirable morbidity in patients with brain tumors who are treated by boron neutron capture radiation therapy.

The use of $[^{10}B]Na_4B_{24}H_{22}S_2$ in the manner described above will effectively reduce these sources of actual and/or potential difficulties of applying boron neutron capture therapy to treatment of human brain tumors, so that such therapy will be of effective clinical usefulness.

DETAILED DESCRIPTION OF THE INVENTION

Slow infusion of $[^{10}B]Na_4B_{24}H_{22}S_2$ provides a prospect for obtaining sufficient absolute concentrations of boron-10 in tumor (>15 μg B/g) and sufficiently high (>5) tumor:blood and tumor:cerebrum boron concentration ratios to be useful for boron neutron capture therapy. Using prior art approaches, such favorable boron concentration ratios are not attainable. Thus $[^{10}B]Na_4B_{24}H_{22}S_2$ should be preferable to $Na_2B_{12}H_{11}SH$ (currently in clinical use) as a boron transport agent for boron neutron capture therapy of brain tumors.

Preliminary study suggests that most of the boron in blood is associated with plasma, not with erythrocytes. Thus, plasma exchanges or plasmaphereses should be useful procedures to precede the irradiation of the neoplasm by neutrons that occurs during $[^{10}B]Na_4B_{24}H_{22}S_2$-mediated boron neutron capture therapy of human malignant gliomas; such procedures would be Performed to minimize radiation damage to normal brain endothelial cells.

Slow uptake of $[^{10}B]Na_4B_{24}H_{22}S_2$ by a tumor should be followed by slow release from the tumor after infusion has ceased. This offers the potential benefit of using a low radiation dose rate to allow repair of damage from the poorly localized low linear energy transfer (LET) radiations associated with boron neutron capture therapy. Table 1 reports the boron-10 concentrations for a number of experiments performed with the dimer material. Referring to Table 1, comparison of experiments 1 and 2 with experiments 7–11 suggests that tumor:blood and tumor:cerebrum boron concentration ratios may prove to be more favorable clinically when $[^{10}B]Na_4B_{24}H_{22}S_2$ is administered very slowly to humans with brain tumors rather than more rapidly over the course of several hours, as $[^{10}B]Na_2B_{12}H11SH$ is now administered in Japan.

EXAMPLE 1

$Cs_4B_{24}H_{22}S_2$ was synthesized from $Cs_2B_{12}H_{11}S$ by the method of Wellum et al, *Inorg. Chem.*, 16, 2120 (1977). The sparsely soluble cesium salts of these two boranes were converted to their highly soluble sodium salts as follows. One hundred mg of the cesium salt was dissolved in 15 ml of warm water with stirring, then passed through an ion-exchange column (1.5×1.0 cm) containing 0.6 g of 100–200 mesh Dowex 50 W-X8. Recovery efficiency of the column, as judged by prompt gamma analysis of boron in aliquots of column inflow and outflow, was >90%. X-ray fluorescence analysis of the sodium salts failed to reveal residual Cs.

Thin layer chromatography (TLC) with 3 M aqueous $NH_4NO_3$: acetonitrile (2:1) on DEAE cellulose plates (Brinkmann, Westbury, N.Y.) was used to detect contamination of $Na_4B_{24}H_{22}S_2$ ($R_f$=0.23) by $Na_2B_{12}H_{11}SH$($R_f$=0.56). The visible spectrum of the blue, non-degassed solution of $2.3\times10^{-4}$ M $Cs_4B_{24}H_{22}S_2$ in the colorless solvent, $5.0\times10^{-3}$ M trifluoroacetic acid in dimethylformamide, had one broad absorbance band which peaked at about 628 nm. The 628 nm absorbance of the solution decreased slowly with a half-life of ~66 days, much longer than that reported originally (~8 days). The initial absorbance of the solution, 0.71, was only two-thirds of the expected absorbance.

ESR of the blue $Cs_4B_{24}H_{22}S_2$ solution was performed with a Varian E-line X-band spectrometer calibrated for field sweep with an aqueous solution of $K_2(SO_3)_2NO$ and for g measurements with a solution of perylene in concentrated sulfuric acid. A single peak was found at g=2.023. The previously reported value was 2.019. The peak-to-peak width of the first derivative of the signal was 18.6 gauss. The signal width at half maximum intensity was 26.0 gauss, slightly greater than the reported value of 19.3 gauss. The 628 nm absorbance and the relative intensity of the ESR signal of the blue solution decreased with time at a constant arithmetic ratio. Other indications that $[B_{24}H_{22}S_2]^{4-}$ was the principal component of the present preparation were the correspondence of the principal infrared absorption bands of the cesium salt of the present preparation with those of $Cs_4B_{24}H_{22}S_2$ and the lack of significant contamination of the sodium salt of the present preparation by $Na_2B_{12}H_{11}SH$ as measured by TLC.

EXAMPLE 2

Aqueous solutions of $[^{10}B]Na_2B_{12}H_{11}SH$ or $[^{10}B]Na_4B_{24}H_{22}S_2$ were infused slowly intraperitoneally [~200 μl capacity osmotic pump, model 2001, Alza Corp., Palo Alto, Calif.] or were injected intraperitoneally promptly into 15–20 g female BALB/cJ mice bearing subcutaneously implanted Harding-Passey (HP) melanomas. In experiment 6 (Table 1), $5.3\times10^{-3}$ M $Na_2S_2O_5$ was added to retard oxidation of $[B_{12}H_{11}SH]^{2-}$. Mice were deeply anesthetized with ether and then killed by exsanguination at times specified in Table 1. The osmotic pumps were designed to function for 219±6 hr, although the precise duration of their infusion in each mouse is unknown. Focal hepatic necrosis and fibrosis which were observed in some mice bearing the rigid cylindrical (3.0×0.7 cm) osmotic pump for ~9 days may have been due in part to direct mechanical pressure on the liver or its vasculature by the osmotic pump.

Tissue and blood specimens in quartz test tubes, with sufficient $H_2O$ added to bring each sample to a total weight of 1.00 g, were analyzed for boron by counting 478 keV gamma photons from the $^{10}B(n,\alpha\gamma)^7Li$ reaction during irradiation by slow neutrons. The results of boron analyses of melanomas, whole blood and whole cerebra are shown in Table 1. The uptake of boron from $[^{10}B]Na_4B_{24}H_{22}S_2$ into a subcutaneous transplanted non-melanotic mouse tumor (a mammary carcinoma originally induced by chronic low-level benzene inhalation in CBA/Ca mice) is comparable to the uptake of boron into the Harding-Passey melanoma when similar doses of the disulfide are administered to mice bearing these tumors via intraperitoneal osmotic pumps. This indicates that the affinity of tumors for $Na_4B_{24}H_{22}S_2$ is not due to the special metabolism of melanin in a tumor.

TABLE 1

Boron Concentrations in Blood, Cerebrum and Melanoma Tumor of Mice From Intraperitoneal Administration of a Sulfhydryl Borane and Its Disulfide

| Experiment No. | No. of Mice | Time[a] (hr) | Dose[b] μgB/gbw | Boron Concentration: Tumor[c] μgB/g | Boron Concentration: Blood[c] μgB/g | Boron Concentration: Cerebrum[c] μgB/g | Concentration Ratios: Tumor:Blood | Concentration Ratios: Tumor:Cerebrum |
|---|---|---|---|---|---|---|---|---|
| Osmotic pump: intraperitoneal infusion | | | | | | | | |
| $Na_4B_{24}H_{22}S_2$ | | | | | | | | |
| 1 | 4 | 216 | 290 ± 20 | 23.9 ± 2.7(4) | 3.6 ± 1.2(4) | 4.0 ± 2.3(2) | 6.6 | 6.0 |
| 2 | 4 | 238 | 266 ± 8 | 23.5 ± 6.9(4) | 4.5 ± 1.4(4) | 5.2 ± 0.4(2) | 5.2 | 4.5 |
| $Na_2B_{12}H_{11}SH$ | | | | | | | | |
| 3 | 5 | 219 | 195 ± 11 | 8.5 ± 2.9(5) | 5.5 ± 3.0(5) | 1.2 ± 1.0(3) | 1.5 | 7.1 |
| 4 | 4 | 234 | 262 ± 11 | 14.1 ± 1.1(3) | 7.7 ± 4.6(4) | 3.2 ± 0.0(2) | 1.8 | 4.4 |

TABLE 1-continued

Boron Concentrations in Blood, Cerebrum and Melanoma Tumor of Mice From Intraperitoneal Administration of a Sulfhydryl Borane and Its Disulfide

| Experiment No. | No. of Mice | Time[a] (hr) | Dose[b] μgB/gbw | Boron Concentration: Tumor[c] μgB/g | Blood[c] μgB/g | Cerebrum[c] μgB/g | Concentration Ratios: Tumor:Blood | Tumor:Cerebrum |
|---|---|---|---|---|---|---|---|---|
| 5 | 4 | 190 | 187 ± 17 | 12.6 ± 1.7(4) | 13.2 ± 6.3(4) | 7.0(1) | 1.0 | 1.8 |
| $Na_2B_{12}H_{11}SH$ with $5.3 \times 10^{-3M}$ $Na_2S_2O_5$ | | | | | | | | |
| 6 | 4 | 219 | 187 ± 15 | 7.9 ± 1.5( ) | 4.9 ± 1.1(4) | 1.0 ± 0.4(2) | 1.6 | 7.9 |
| Prompt intraperitoneal injection | | | | | | | | |
| $Na_4B_{24}H_{22}S_2$ | | | | | | | | |
| 7 | 8 | 6 | 36 ± 2 | 10.6 ± 1.6(5) | 12.1 ± 1.5(8) | 1.5 ± 0.4(4) | 0.9 | 7.1 |
| 8 | 6 | 12 | 36 ± 2 | 12.1 ± 3.1(6) | 4.9 ± 0.7(5) | 0.8 ± 0.6(3) | 2.5 | 15.1 |
| 9 | 3 | 12 | 30.2 ± 1.8 | 6.4 ± 3.4(3) | 4.3 ± 5.3(3) | 5.9(1) | 1.5 | 1.1 |
| 10 | 4 | 24 | 36 ± 2 | 9.0 ± 2.6(4) | 2.8 ± 0.5(4) | 1.3 ± 0.6(2) | 3.2 | 6.9 |
| 11 | 3 | 24 | 30.9 ± 1.7 | 9.8 ± 3.3(3) | 1.6 ± 1.6(3) | 4.1 ± 5.7(2) | 6.1 | 2.4 |
| $Na_2B_{12}H_{11}SH$ | | | | | | | | |
| 12 | 3 | 6 | 35.4 ± 1.3 | 8.7 ± 9.9(3) | 3.8 ± 9.9(3) | 3.8 ± 3.4(3) | 2.3 | 2.3 |
| 13 | 3 | 12 | 35.5 ± 2.2 | 5.5 ± 4.8(3) | 5.5 ± 4.8(3) | 0.9 ± 1.6(3) | 1.0 | 6.1 |
| 14 | 3 | 24 | 34.5 ± 1.0 | 6.3 ± 2.2(3) | 6.3 ± 2.2(3) | 4.9 ± 3.8(3) | 1.0 | 1.3 |

[a]Time after start of infusion or after prompt injection
[b]Mean ± standard deviation (Experiment Nos. 7, 8, 10: mean ± estimated range)
[c]Mean ± standard deviation (number of tissues)

We claim:

1. A method of utilizing boron neutron capture therapy for treatment of brain tumors which comprises slowly infusing a radiotherapeutically effective amount of $[^{10}B]Na_4B_{24}H_{22}S_2$ at an infusion rate of approximately 1 μg $^{10}B$ per gram of body weight per hour into the patient and thereafter exposing the diseased area to neutron irradiation.

2. The method of claim 1 wherein the $[^{10}B]Na_4B_{24}H_{22}S_2$ is slowly infused over a period of at least one week to yield high tumor/blood and tumor/cerebrum concentrations.

3. The method of claim 1 wherein $[^{10}B]Na_4B_{24}H_{22}S_2$ is slowly infused using a dosage of about 200 μg of $^{10}B$ per gm of body weight.

* * * * *